United States Patent [19]

Soula

[11] 4,189,389
[45] Feb. 19, 1980

[54] NOVEL ALKENYL SUCCINIMIDES AND PROCESS FOR THEIR PREPARATION

[75] Inventor: Gerard Soula, Meyzieu, France

[73] Assignee: Orogil, Courbevoie, France

[21] Appl. No.: 2,240

[22] Filed: Jan. 9, 1979

[30] Foreign Application Priority Data

Jan. 11, 1978 [FR] France .................. 78 00625

[51] Int. Cl.$^2$ .............................. C10M 1/38
[52] U.S. Cl. .................. 252/47.5; 252/51.5 A; 260/326.5 S
[58] Field of Search ............ 252/47.5, 51.5 A; 260/326.5 S

[56] References Cited

U.S. PATENT DOCUMENTS

| | | | |
|---|---|---|---|
| 3,036,088 | 5/1962 | Harris, Jr. | 260/326.5 S X |
| 3,219,666 | 11/1965 | No rman et al. | 252/51.5 A X |
| 3,231,587 | 1/1966 | Rense | 260/346.8 |
| 3,306,907 | 2/1967 | McNinch et al. | 260/326.3 |
| 3,309,316 | 3/1967 | McNinch et al. | 252/47.5 |
| 3,390,086 | 6/1968 | O'Halloran | 252/47.5 |
| 3,894,043 | 7/1975 | Moser et al. | 260/326.5 S |
| 3,912,764 | 10/1975 | Palmer, Jr. | 260/346.8 |
| 4,081,388 | 3/1978 | Soula et al. | 252/51.5 A |
| 4,094,802 | 6/1978 | Soula et al. | 252/51.5 A |

FOREIGN PATENT DOCUMENTS

| | | | |
|---|---|---|---|
| 805486 | 1/1974 | Belgium | 260/346.8 |
| 2042558 | 12/1971 | France . | |
| 1356802 | 6/1974 | United Kingdom . | |
| 1480453 | 7/1977 | United Kingdom . | |

*Primary Examiner*—Andrew Metz

[57] ABSTRACT

New lubricant additive compositions containing at least one alkenyl succinimide of the formula:

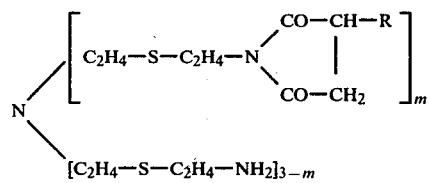

in which R is an alkenyl group of from about 20 to 200 carbon atoms and m is a whole number from 1 to 3.

They are produced from the reaction of an alkenyl succinic anhydride comprising a $C_{20}$–$C_{200}$ alkenyl group and tris(5-amino-3-thia-pentyl)amine. The additive compositions are useful in lubricating oils.

9 Claims, No Drawings

NOVEL ALKENYL SUCCINIMIDES AND PROCESS FOR THEIR PREPARATION

BACKGROUND OF THE INVENTION

The present invention relates to novel compositions based on alkenyl succinimides derived from tris(5-amino-3-thia-pentyl)amine, a novel process for their preparation, and to lubricating oils containing said novel alkenyl succinimides as additives.

It is known to react the alkenyl succinic anhydrides with aliphatic monoamines, aromatic amines, heterocyclic amines, etc., alkylidene polyamines, polyoxyalkylidene amines, etc., and to use the alkenyl succinimides thus obtained as additives for lubricating oils.

By the present invention, new compositions, in the nature of lubricant additives, are provided comprising new alkenyl succinimides which impart improved detergent-dispersant and anti-rust properties to lubricating oils.

It is, accordingly, an object of the present invention to provide novel lubricant additive compositions based on alkenyl succinimides derived from alkenyl succinic anhydrides and tris(5-amino-3-thia-pentyl)amine which impart to lubricating oils excellent performance characteristics.

It is a further object of the present invention to provide novel processes for producing the new lubricant additive compositions of the invention.

It is also an object of the present invention to provide novel lubricants containing the novel lubricant additive compositions of the present invention.

Further objects of the present invention will be apparent to those skilled in the art from the present disclosure.

GENERAL DESCRIPTION OF THE INVENTION

The new compositions which form an object of the present invention comprise at least one alkenyl succinimide of the formula:

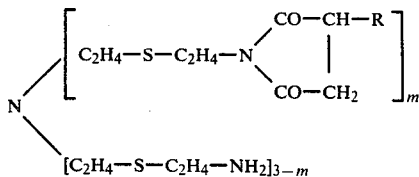

in which R represents an alkenyl group containing from about 20 to 200 carbon atoms and m is a whole number from 1 to 3.

The novel compositions of the invention may be prepared by reacting an alkenyl succinic acid anhydride, in which the alkenyl group contains from about 20 to 200 carbon atoms, with tris(5-amino-3-thia-pentyl)amine at a temperature of between 120° and 230° C., preferably between 140° and 180° C., in a ratio of number of amine equivalents to number of acid equivalents of between about 0.4 and 0.6.

By number of amine equivalents is understood to refer to the number of —$NH_2$ units of the tris(5-amino-3-thia-pentyl)amine. By number of acid equivalents it is understood to mean the number of $$\overset{O}{\underset{\|}{-C-}}$$

units of the alkenyl succinic anhydride used. Theoretically, one equivalent of amine is required for two equivalents of acid in order to form a succinimide ring.

The reaction may be carried out in the presence of a diluent in order to decrease the viscosity of the reaction medium. Said diluent will preferably be selected from among lubricating oils which can serve as base oils in lubricating compositions, examples of which base oils will be given below.

The alkenyl succinic anhydrides used are prepared in known manner, for instance, by thermal condensation (see U.S. Pat. No. 3,306,907) of maleic anhydride on a polyolefin of average molecular weight of between about 400 and 4000. The said polyolefin is selected from oligomers or polymers of $C_2$–$C_{30}$ olefins, possibly branched, or the copolymers of the said olefins with each other or with diene or vinylaromatic comonomers. Among these polyolefins, mention may be made preferably of oligomers of $C_2$–$C_{20}$ α-monoolefins, such as oligomers of ethylene, propylene, butene-1, of isobutene, of 3-cyclohexyl-butene-1, or 2-methyl-5-propyl-hexene-1, the copolymers of these α-olefins with each other or with internal olefins, as well as the copolymers of isobutene with a comonomer selected from among butadiene, styrene, hexadiene-1,3, or the conjugated or non-conjugated dienes and trienes.

The condensation operation can also be carried out in the presence of chlorine (see U.S. Pat. No. 3,231,587 and Belgian patent No. 805,486), iodine (British patent No. 1,356,802), or bromine (French patent application No. 74.18915, filed on May 31, 1974, in the name of the French corporation Rhone-Progil). This operation can also be carried out starting from monochlorinated or monobrominated polyolefins, as indicated in the French patent published under No. 2,042,558.

The tris(5-amino-3-thia-pentyl)amine used can be prepared by the action of tris(ethanethiol)amine on aziridine in a molar ratio of aziridine to tris(ethanethiol)amine of between about 3 and 3.5, and preferably between 3 and 3.2, at a temperature of between 30° and 85° C., and preferably between 45° and 80° C., followed by separation of the tris(5-amino-3-thia-pentyl)amine obtained. This process is disclosed in my copending United States application, entitled "Tris(5-amino-3-thia-pentyl)amine and Method of Preparing Same", Ser. No. 2,239, filed concurrently.

The reaction between the aziridine and the tris(ethanethiol)amine is carried out in the presence of a solvent such as methanol, ethanol, chloroform, methylene chloride, chlorobenzene, etc.; it takes about 0.5 to 3 hours.

The present invention is also directed to lubricating oils which are improved by the addition of 1 to 10 percent of their weight of the additive compositions of the invention, contributing their detergent-dispersant, anti-rust, and anti-foam properties to the said oils.

The lubricating oils which can be used may be selected from among very different lubricating oils, such as naphthene-base, paraffin-base, and mixed-based lubricating oils, other hydrocarbon lubricants, for instance, lubricating oils derived from coal products, and synthetic oils, such as alkylene polymers, polymers of the alkylene oxide type and their derivatives, including the alkylene oxide polymers prepared by polymerizing alkylene oxide in the presence of water or alcohols, such as ethyl alcohol, dicarboxylic acid esters, liquid esters of acids of phosphorus, alkyl benzenes, dialkyl benzenes, polyphenyls, alkyl biphenyl ethers, and polymers of silicon.

The quantity of new additives to be added is a function of the future use of the lubricating oil which is to be improved. Thus, for gasoline motor oil, the amount of additive to be added will desirably be from about 1 to 7 percent, and for a diesel motor oil, it will desirably be from about 4 to 10 percent.

The improved lubricating oils may also contain antioxidant and anti-corrosion adjuvants, etc.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Into a 250 cc. three-neck flask provided with mechanical agitator, a thermometer, and a dropping funnel, there are introduced 120 g. of polyisobutenyl succinic anhydride, obtained from the reaction of maleic anhydride and polyisobutene, having an average molecular weight of about 900. The acid number of this alkenyl succinic anhydride is 70 mg. of potassium hydroxide per gram. The product is heated to 155° C. 8.3 g. of tris(5-amino-3-thia-pentyl)amine are then introduced during the course of 30 minutes. After addition of the amine, the mixture is placed under vacuum (20 mm. of mercury) at 155° C. for 2 hours. A clear product is obtained, composed essentially of a tris-succinimide derived from the amine introduced. The chemical composition of this product is:

|  | % Measured | % Theoretical |
|---|---|---|
| nitrogen | 1.05 | 1.10 |
| sulfur | 1.92 | 1.91 |

The tris(5-amino-3-thia-pentyl)amine used can be prepared in the following manner:

Synthesis of tris(5-amino-3-thia-pentyl)amine

Into a 500 cc. three-neck flask provided with a mechanical agitator, a thermometer, and a dropping funnel, there were introduced 19.7 g., namely, 0.1 mol, of tris(thioethanol)amine dissolved in 250 cc. of methanol. The mixture was heated to 45° C. Thereupon, 0.3 mol of aziridine (15.5 ml.) diluted in 20 cc. of methanol was added over the course of 30 minutes by means of the dropping funnel.

The mixture was then brought to the reflux temperature of the methanol (64° C. for 3 hours) and the methanol was finally evaporated. There were obtained 32 g. of an oily product having the following chemical composition:

|  | % Measured | % Theoretical |
|---|---|---|
| sulfur | 29.5 | 29.4 |
| nitrogen | 17.1 | 17.2 |
| carbon | 44.3 | 44.1 |
| hydrogen | 9.15 | 9.2 |

EXAMPLE 2

Into a one-liter, three-neck flask provided with a mechanical agitator, a thermometer, and a dropping funnel, there were introduced 600 g. of polyisobutenyl succinic anhydride, obtained from the reaction of maleic anhydride and polyisobutene, of an average molecular weight of about 900. The acid number of this alkenyl succinic anhydride is 70 mg. of KOH/g. The product was heated to 155° C. Thereupon, 120 g. of tris(5-amino-3-thia-pentyl)amine were introduced during the course of 30 minutes. After addition of the amine, the mixture was placed under vacuum (20 mm. of mercury) at 160° C. for 2 hours. A clear product was obtained, consisting essentially of a monosuccinimide derived from the amine introduced. The chemical composition of this product was as follows:

|  | % Determined | % Theoretical |
|---|---|---|
| sulfur | 4.8 | 4.9 |
| nitrogen | 2.7 | 2.8 |

EXAMPLE 3

The products of the invention obtained in accordance with the above examples were tested with respect to their dispersing properties in lubricants. The study of the dispersive power was carried out in accordance with the spot method described in Volume 1 of the book by A. Schilling, "Motor Oils and the Lubrication of Engines," 1962 edition, pages 89–90. The method was carried out on the basis of 20 g. of SAE 30 oil to which there have been added 5 g. of sludge coming from a Petter AV₁ engine and containing about 2 percent of carbonaceous matter.

The following formulation had been previously added to the SAE 30 oil (the quantities of the different additives are given per kilogram of oil):

40 g. of dispersant obtained in Examples 1 or 2;
30 mmols of calcium alkyl benzene sulfonate;
30 mmols of super-alkalinized calcium alkyl phenate; and
15 mmols of zinc dihexyldithiophosphate.

The mixture of oil containing the above compositions and sludge was separated into five fractions, which were agitated and subjected to the following five heat treatments:

one fraction subjected to heating at 50° C. for 10 minutes;

one fraction subjected to heating at 200° C. for 10 minutes;

one fraction subjected to heating at 250° C. for 10 minutes;

one fraction subjected to heating at 50° C. for 10 minutes in the presence of 1 percent water;

one fraction subjected to heating at 200° C. for 10 minutes in the presence of 1 percent water.

A drop of each mixture obtained after heat treatment is deposited on filter paper.

The rating was effected at the end of 48 hours. For each spot, the percentage of product dispersed with respect to the spot of oil is calculated by forming the ratio of the respective diameters of the spot of oil and the dispersed product. The higher the percentage of dispersed product, the better the dispersion with respect to the sludge. The ratings appear in the table appearing below.

EXAMPLE 4

The anti-rust properties of the products of Examples 1 and 2 were tested in SAE 30 oil to which there had been added the formulation of the preceding example, namely, for 1 kg. of oil:

40 g. of one of products of Examples 1 or 2;

30 mmols of calcium alkyl benzene sulfonate;

30 mmols of super-alkalinized calcium alkyl phenate; and 15 mmols of zinc dihexyldithiophosphate.

The principle of the test consists of adding to the oil under study the products which can be found in the blow-by gases and which act in the formation of rust on the valve tappet and stem assembly and immersing a part which is a portion of the said assembly for a certain period of time in the mixture thus formed. The rust formed is rated visually.

The test is carried out by:

introduction of 700 g. of oil into a flask and heating to 50° C. with agitation;

successive addition, when the temperature is stabilized, of 20 cc. of an aqueous solution of 30 percent formaldehyde, 4.5 cc. of methanol, 5 cc. of a 50/50 mixture of dichloroethane and dibromoethane, and 8.5 cc. of an aqueous solution of 78.5 percent nitric acid;

immersion for 19 hours of a part of the valve tappet-stem assembly.

If there is no attack, the product is given a rating of 20; when the attack is very extensive, it is given a rating of zero. The results of the ratings are set forth in the table appearing below.

EXAMPLE 5

The anti-foam properties of the products of Examples 1 and 2 were measured, in accordance with ASTM Standard D 892.63, in the SAE 30 oil to which there has been added the formulation indicated in Examples 3 and 4.

The results of the ratings appear in the table below.

By way of comparison, there are set forth in the table appearing below the results of the tests of the dispersing, anti-rust and anti-foam properties, obtained under the conditions described in Examples 3 to 5 on the following succinimides, namely:

I. The tris(polyisobutenyl succinimide) (PIBSA) derived from tris(6-amino-3-oxa-hexyl)amine and a PIBSA of an acid number of 74, obtained by condensation of maleic anhydride and a polyisobutene of a molecular weight close to 1000.

II. The bis(polyisobutenyl succinimide) (PIBSA) from triethylene tetramine and a PIBSA of an acid number of 74, obtained by condensation of maleic anhydride and a polyisobutene of a molecular weight of close to 1000.

TABLE

| Products | Performances | | |
|---|---|---|---|
| | Dispersion | Anti-rust | Anti-foam |
| Example 1 | 450 | 18 | 10–05 |
| Example 2 | 470 | 19 | 10–05 |
| Comparison: | | | |
| I Comparison (above) | 390 | 12 | 20–50 |
| II Comparison (above) | 320 | 9 | 580–450 |

As can be seen from the foregoing table, the novel compositions of the present invention have excellent dispersion, anti-rust, and anti-foam properties when employed in lubricants.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A novel composition based on alkenyl succinimide, comprising at least one alkenyl succinimide of the formula:

$$N\left[C_2H_4-S-C_2H_4-N\begin{array}{c}CO-CH-R\\ \phantom{xx}|\\ CO-CH_2\end{array}\right]_m$$
$$[C_2H_4-S-C_2H_4-NH_2]_{3-m}$$

in which R represents an alkenyl group containing from about 20 to 200 carbon atoms and m is a whole number from 1 to 3.

2. A novel composition according to claim 1, wherein R is a polyisobutenyl group.

3. A novel process of preparing a composition according to claim 1, which process comprises reacting an alkenyl succinic acid anhydride in which the alkenyl group contains from about 20 to 200 carbon atoms, with tris(5-amino-3-thia-pentyl)amine, in a ratio of number of equivalents of amine to number of equivalents of acid of between about 0.4 and 0.6, at a temperature between about 120° and 230° C.

4. A process according to claim 3, wherein the alkenyl group is a polyisobutenyl group.

5. A process according to claim 3, wherein the temperature is between about 140° and 180° C.

6. A novel lubricating composition, having desirable dispersion, anti-rust and anti-foam properties, comprising an oil containing between about 1 and 10 percent by weight of a novel lubricant additive composition according to claim 1.

7. A novel lubricating composition, having desirable dispersion, anti-rust and anti-foam properties, comprising an oil containing between about 1 and 10 percent by weight of a novel lubricant additive composition according to claim 1.

8. A gasoline engine oil, having desirable dispersion, anti-rust and anti-foam properties, containing between about 1 and 7 percent by weight of a novel lubricant additive composition according to claim 1.

9. A novel diesel engine oil having desirable dispersion, anti-rust and anti-foam properties containing between about 4 and 10 percent by weight of a novel lubricating additive composition according to claim 1.

* * * * *

UNITED STATES PATENT AND TRADEMARK OFFICE
CERTIFICATE OF CORRECTION

PATENT NO. : 4,189,389
DATED : February 19, 1980
INVENTOR(S) : Gerard Soula

It is certified that error appears in the above–identified patent and that said Letters Patent are hereby corrected as shown below:

Column 6, line 60, delete "1" and replace with -- 2 --.

Signed and Sealed this

Twentieth Day of May 1980

[SEAL]

Attest:

SIDNEY A. DIAMOND

Attesting Officer     Commissioner of Patents and Trademarks